(12) United States Patent
Malavalli et al.

(10) Patent No.: US 10,821,158 B2
(45) Date of Patent: Nov. 3, 2020

(54) POLYALKYLENE OXIDE VALERATE HEMOGLOBIN CONJUGATES

(71) Applicant: Sangart, Inc., San Diego, CA (US)

(72) Inventors: Ashok Malavalli, San Diego, CA (US); Gnel Mkrtchyan, Cody, WY (US); Kim D. Vandegriff, San Diego, CA (US)

(73) Assignee: William Schindler, Santa Fe, NM (US)

( * ) Notice: Subject to any disclaimer, the term of this patent is extended or adjusted under 35 U.S.C. 154(b) by 207 days.

(21) Appl. No.: 14/777,261

(22) PCT Filed: Mar. 17, 2014

(86) PCT No.: PCT/US2014/030569
§ 371 (c)(1),
(2) Date: Sep. 15, 2015

(87) PCT Pub. No.: WO2014/145755
PCT Pub. Date: Sep. 18, 2014

(65) Prior Publication Data
US 2016/0022783 A1 Jan. 28, 2016

Related U.S. Application Data

(60) Provisional application No. 61/801,016, filed on Mar. 15, 2013.

(51) Int. Cl.
*A61K 38/42* (2006.01)
*A61K 47/60* (2017.01)
*C07K 14/805* (2006.01)
*A61K 38/00* (2006.01)

(52) U.S. Cl.
CPC ............. *A61K 38/42* (2013.01); *A61K 47/60* (2017.08); *C07K 14/805* (2013.01); *A61K 38/00* (2013.01)

(58) Field of Classification Search
CPC .................................................. C07K 14/805
See application file for complete search history.

(56) References Cited

U.S. PATENT DOCUMENTS

| | | | |
|---|---|---|---|
| 4,529,719 A | 7/1985 | Tye | |
| 4,857,636 A | 8/1989 | Hsia | |
| 5,234,903 A | 8/1993 | Nho et al. | |
| 5,250,665 A | 10/1993 | Kluger et al. | |
| 5,296,465 A | 3/1994 | Rausch et al. | |
| 5,650,388 A | 7/1997 | Shorr et al. | |
| 6,432,918 B1 * | 8/2002 | Winslow | A61K 38/42 424/529 |
| 6,828,401 B2 | 12/2004 | Nho et al. | |
| 6,844,317 B2 | 1/2005 | Winslow et al. | |
| 7,005,414 B2 | 2/2006 | Bamikol et al. | |
| 7,501,499 B2 | 3/2009 | Acharya et al. | |
| 2003/0153491 A1 | 8/2003 | Winslow et al. | |
| 2004/0014641 A1 | 1/2004 | Bamikol | |
| 2004/0072729 A1 | 4/2004 | Kwang et al. | |
| 2006/0135753 A1 | 6/2006 | Acharya et al. | |
| 2006/0234915 A1 | 10/2006 | Winslow | |
| 2007/0049517 A1 | 3/2007 | Bamikol | |

FOREIGN PATENT DOCUMENTS

| | | |
|---|---|---|
| EP | 0 206 448 A1 | 12/1986 |
| KR | 2000-0061432 A | 10/2000 |
| WO | 91/07190 A1 | 5/1991 |
| WO | 03/094953 A1 | 11/2003 |
| WO | 2004/012773 A1 | 2/2004 |
| WO | 2010/144629 A1 | 12/2010 |
| WO | 2013/151776 A1 | 10/2013 |

OTHER PUBLICATIONS

Conover, C.D., et al. 1999 Art. Cells, Blood Subs., and Immob. Biotech. 27(2): 93-107. (Year: 1999).*
Mero, A., et al. 2011 Covalent Conjugation of Poly(Ethylene Glycol) to Proteins and Peptides: Strategies and Methods. In: Mark S. (eds) Bioconjugation Protocols. Methods in Molecular Biology (Methods and Protocols), vol. 751: pp. 95-129. (Year: 2011).*
Laysan I (mPEG-SVA product sheet: 2 pages total); retrieved from the internet Dec. 14, 2017. (Year: 2017).*
Laysan II (Benefit of using the SVA over the SCM: 1 page total); retrieved from the internet Dec. 14, 2017. (Year: 2017).*
Anjaneyulu, P.S.R., et al. 1987 Int. J. Peptide Protein Res. 30: 117-124. (Year: 1987).*
Hu, T., et al., "Influence of Intramolecular Cross-Links on the Molecular, Structural and Functional Properties of PEGylated Haemoglobin," Biochemical Journal, Feb. 2007, pp. 143-151, vol. 402, No. 1.
Suo, X., et al., "Solid Phase Pegylation of Hemoglobin," Artificial Cells, Blood Substitutes, and Immobilization Biotechnology, 2009, pp. 147-155, vol. 37, No. 4.
Supplementary European Search Report issued for European Application No. EP 14765388.5, dated Oct. 6, 2016, 10 pages.
White, F. L., et al., "Effects of Crosslinking on the Thermal Stability of Hemoglobin. I. The Use of bis (3,5-dibromosalicyl) Fumarate," Archives of Biochemistry and Biophysics, Oct. 1987, pp. 51-57, vol. 258, No. 1.
Blumenstein, J., et al., "Experimental Transfusion of Dextran-Hemoglobin," Blood Substitutes and Plasma Expanders, 1978, pp. 205-212, vol. 19.
Doherty, D. H., et al., "Rate of Reaction with Nitric Oxide Determines the Hypertensive Effect of Cell-Free Hemoglobin," Nature Biotechnology, Jul. 1998, pp. 672-676, vol. 16, No. 7.
Dust, J. M., et al., "Proton NMR Characterization of Poly(ethylene glycols) and Derivatives," Macromolecules, 1990, pp. 3742-3746, vol. 23, No. 16.
Eich, R. F., et al., "Mechanism of NO-Induced Oxidation of Myoglobin and Hemoglobin," Biochemistry, 1996, pp. 6976-6983, vol. 35, No. 22.

(Continued)

*Primary Examiner* — Marsha Tsay
(74) *Attorney, Agent, or Firm* — Lewis Rice LLC

(57) ABSTRACT

The present invention relates generally to polyethylene glycol (PEG) conjugated hemoglobins made by conjugation of succinimidyl-valerate activated polyethylene glycol to primary amines and N-terminal valines of the hemoglobin.

19 Claims, 4 Drawing Sheets

(56) References Cited

OTHER PUBLICATIONS

Foot, J. S., et al., "Hemoglobin bis-tetramers via Cooperative Azide-Alkyne Coupling," Chemical Communications, 2009, pp. 7315-7317, vol. 47.

Furchgott, R. F., "The Role of Endothelium in the Responses of Vascular Smooth Muscle to Drugs," Annual Review of Pharmacology and Toxicology, 1984, pp. 175-197, vol. 24.

Hess, J. R., et al., "Pulmonary and Systemic Hypertension After Hemoglobin Administration," Poster Session IV: Transfusion, Meeting Abstract 1414, Blood, 1991, p. 356A, vol. 78.

Hess, J. R., et al., "Systemic and Pulmonary Hypertension After Resuscitation with Cell-Free Hemoglobin," Journal of Applied Physiology, Apr. 1993, pp. 1769-1778, vol. 74, No. 4.

Hu, T., et al., "Influence of the Chemistry of Conjugation of Poly(ethylene glycol) to Hb on the Oxygen-binding and Solution Properties of the PEG-Hb Conjugate," The Biochemical Journal, Dec. 15, 2005, pp. 555-564, vol. 392, Part 3.

Iwashita, Y., et al., "Renal Toxicity of Hemoglobin Derivatives as Blood Substitute," Organ-Directed Toxicity Chemical Indices and Mechanisms, Proceedings of the Symposium on Chemical Indices and Mechanisms of Organ-Directed Toxicity, Presented in Barcelona, Spain, Mar. 4-7, 1981, pp. 97-101.

Kilbourn, R. G., et al., "Cell-Free Hemoglobin Reverses the Endotoxin-Mediated Hyporesponsivity of Rat Aortic Rings to alpha-adrenergic Agents," Biochemical and Biophysical Research Communications, Feb. 1994, pp. 155-162, vol. 199, No. 1.

Lemon, D. D., et al., "Control of the Nitric Oxide-Scavenging Activity of Hemoglobin," Biotechnology, 1996, p. 378, vol. 24.

MacDonald, V. W., et al., "Vasoconstrictor Effects in Isolated Rabbit Heart Perfused with bis(3,5-dibromosalicyl) Fumarate Cross-Linked Hemoglobin (alpha alpha Hb)," Artificial Cells, Blood Substitutes, and Immobilization Biotechnology, 1994, pp. 565-575, vol. 22, No. 3.

Manjula, B. N., et al., "Site-Specific PEGylation of Hemoglobin at Cys-93(beta): Correlation Between the Colligative Properties of the PEGylated Protein and the Length of the Conjugated PEG Chain," Bioconjugate Chemistry, Mar.-Apr. 2003, pp. 464-472 vol. 14, No. 2.

Muldoon, S. M., et al., "Hemoglobin-Induced Contraction of Pig Pulmonary Veins," The Journal of Laboratory and Clinical Medicine, Dec. 1996, pp. 579-584, vol. 128, No. 6.

Rohlfs, R. J., et al., "Arterial Blood Pressure Responses to Cell-Free Hemoglobin Solutions and the Reaction with Nitric Oxide," The Journal of Biological Chemistry, May 1998, pp. 12128-12134, vol. 273, No. 20.

Vandegriff, K. D., et al., "Hemoglobin—Oxygen Equilibrium Binding: Rapid-Scanning Spectrophotometry and Singular Value Decomposition," Methods in Enzymology, 1994, pp. 460-485, vol. 232.

Vandegriff, K. D., et al., "Hemoglobin-Oxygen Equilibrium Curves Measured During Enzymatic Oxygen Consumption," Analytical Biochemistry, Feb. 1998, pp. 107-116, vol. 256, No. 1.

Vandegriff, K. D., et al., "Kinetics of NO and O2 Binding to a Maleimide Poly(ethylene glycol)-conjugated Human Haemoglobin," The Biochemical Journal, Aug. 2004, pp. 183-189, vol. 382, Part 1.

Vandegriff, K. D., et al., "MP4, A New Nonvasoactive PEG-Hb Conjugate," Transfusion, Apr. 2003, vol. 43, pp. 509-516.

Walder, J. A., et al., "Diaspirins That Cross-Link Beta Chains of Hemoglobin: bis(3,5-dibromosalicyl) Succinate and bis(3,5-dibromosalicyl) Fumarate," Biochemistry, Oct. 1979, pp. 4265-4270, vol. 18, No. 20.

Wang, D., et al., "Polymer-mediated Immunocamouflage of Red Blood Cells: Effects of Polymer Size on Antigenic and Immunogenic Recognition of Allogeneic Donor Blood Cells," Science China Life Sciences, Jul. 2011, pp. 589-598, vol. 54, No. 7.

Winslow, R. M., "alphaalpha-Crosslinked Hemoglobin: Was Failure Predicted by Preclinical Testing?" Vox Sanguinis, 2000, pp. 1-20, vol. 79, No. 1.

Winslow, R. M., et al., "Oxygen Equilibrium Curve of Normal Human Blood and Its Evaluation by Adair's Equation," The Journal of Biological Chemistry, Apr. 1977, pp. 2331-2337, vol. 252, No. 7.

Winslow, R. M., et al., "Vascular Resistance and the Efficacy of Red Cell substitutes in a Rat Hemorrhage Model," Journal of Applied Physiology, Sep. 1998, pp. 993-1003, vol. 85, No. 3.

Yang, Y., et al., "Efficient CuAAC Click Formation of Functional Hemoglobin bis-tetramers," Chemical Communications, 2010, pp. 7557-7559, vol. 46, No. 40.

Zalipsky, S., et al., "Attachment of Drugs to Polyethylene Glycols," European Polymer Journal, 1983, pp. 1177-1183, vol. 19, No. 12.

Chatterjee, R., et al., "Isolation and Characterization of a New Hemoglobin Derivative Cross-Linked Between the Alpha Chains (Lysine 99 Alpha 1—Lysine 99 Alpha 2)," The Journal of Biological Chemistry, Jul. 1986, pp. 9929-9937, vol. 261, No. 21.

Guarnone, R., et al., "Performance Characteristics of Hemox-Analyzer for Assessment of the Hemoglobin Dissociation Curve," Haematologica, Sep.-Oct. 1995, pp. 426-430, vol. 80, No. 5.

Li, D., et al., "Non-Conservative Surface Decoration of Hemoglobin: Influence of Neutralization of Positive Charges at PEGylation Sites on Molecular and Functional Properties of PEGylated Hemoglobin," Biochimica et Biophysica Acta, 2008, pp. 1395-1401, vol. 1784.

Tsuchida, H., et al., "An Approach to the Artificial Blood," Journal of Artificial Organs, 1990, pp. 1552-1558, vol. 19, Issue 6.

Winslow, R. M., "MP4, A New Nonvasoactive Polyethylene Glycol-Hemoglobin Conjugate," Artificial Organs, Sep. 2004, pp. 800-806, vol. 28, Issue 9.

\* cited by examiner

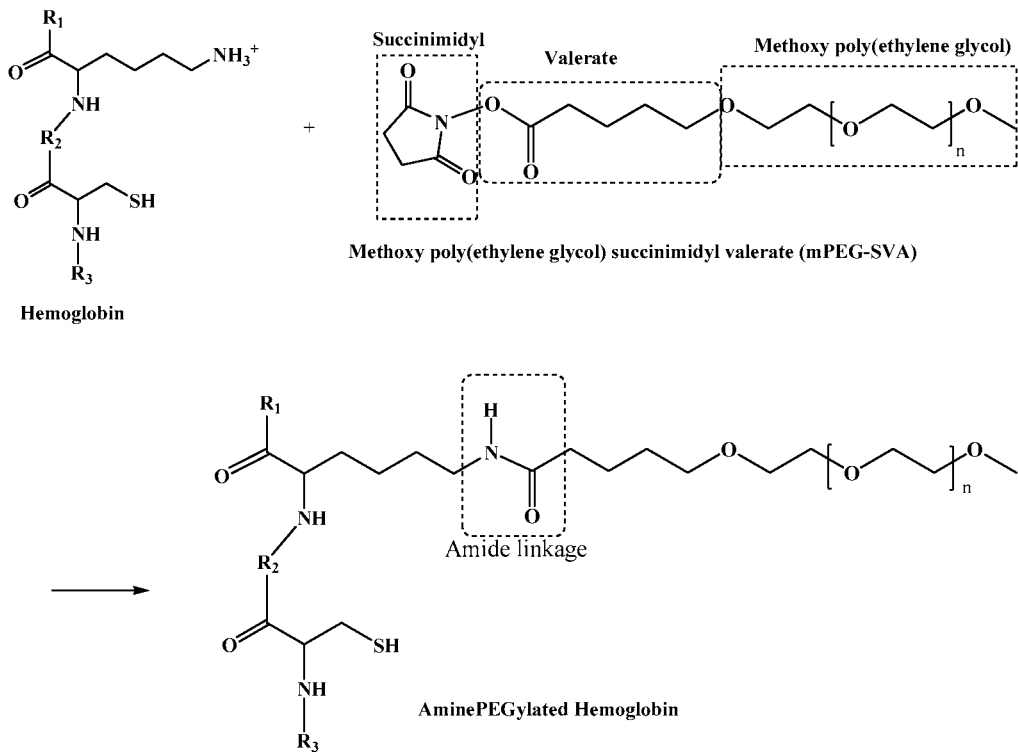
Figure 1: Scheme of SVA-PEGylation reaction
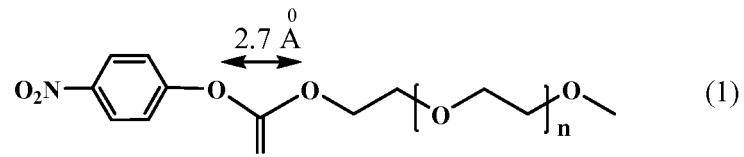
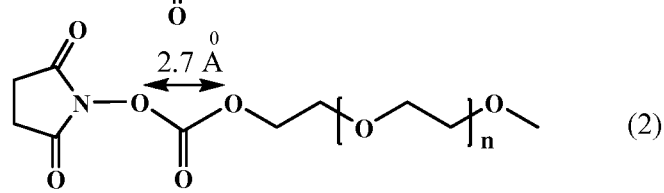
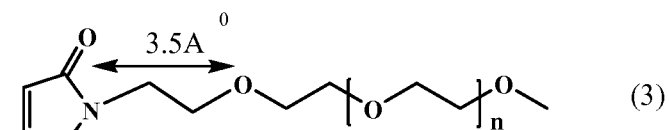
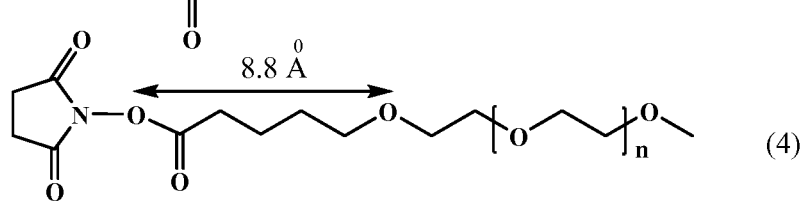
Figure 2. Chemical structures and bond lengths for (1) NPC-PEG, (2) SC-PEG, (3) MalPEG, and (4) SVA-PEG. Arrows show the distance of PEG backbone from the active group.

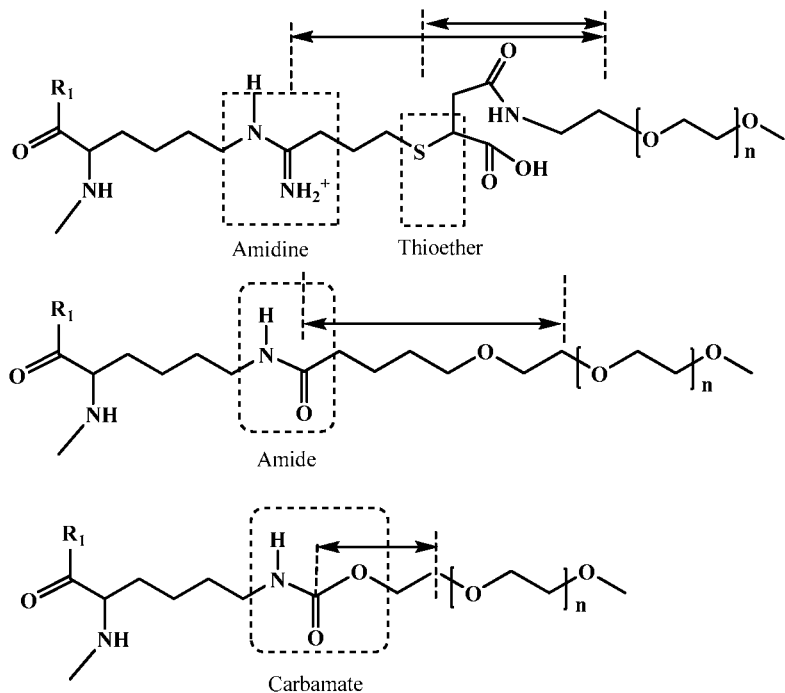
Figure 3: Arrows show the distance between linkage and PEG backbone for MalPEG (top), SVA-PEG (middle), and SC-PEG (bottom).
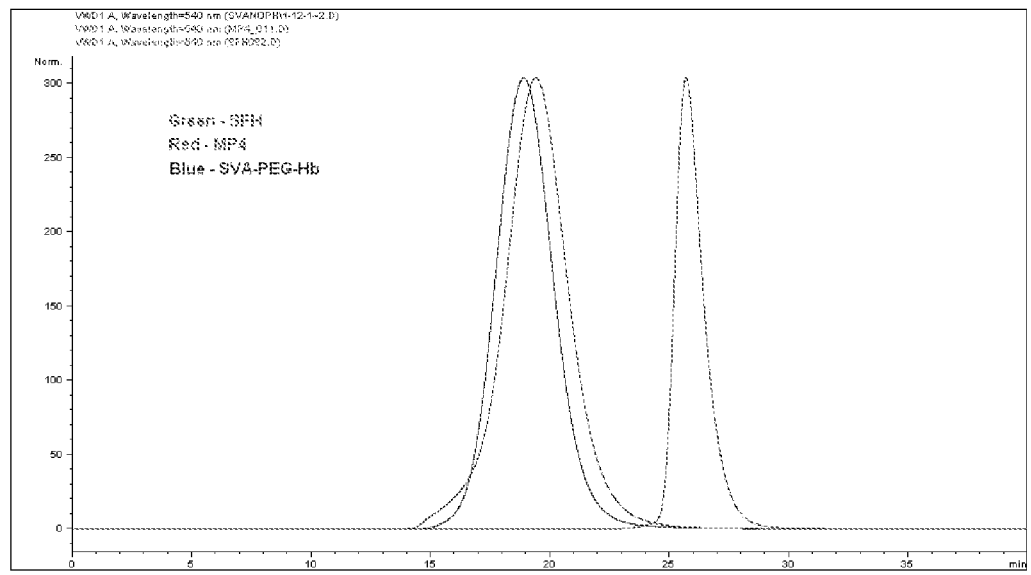
Figure 4: LC analysis of SVA-PEG-Hb compared to thiolated, Mal-PEG-Hb.

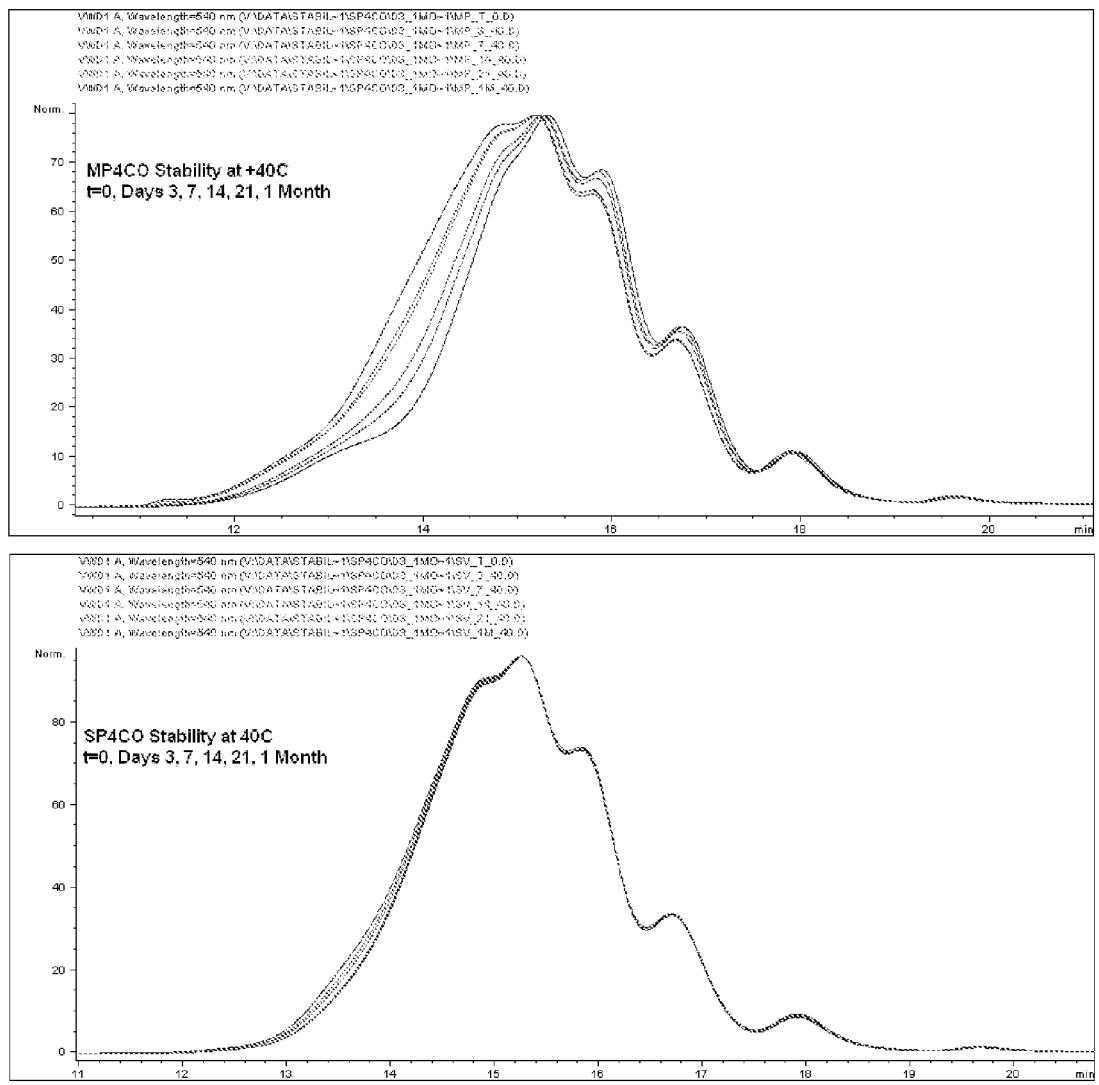
Figure 5: LC under dissociating conditions (0.9M $MgCl_2$) analysis of MALPEG-Hb (MP4CO, top) versus SVA-PEG-Hb (SP4CO, bottom) under accelerated stability conditions at 40°C for up to one month.

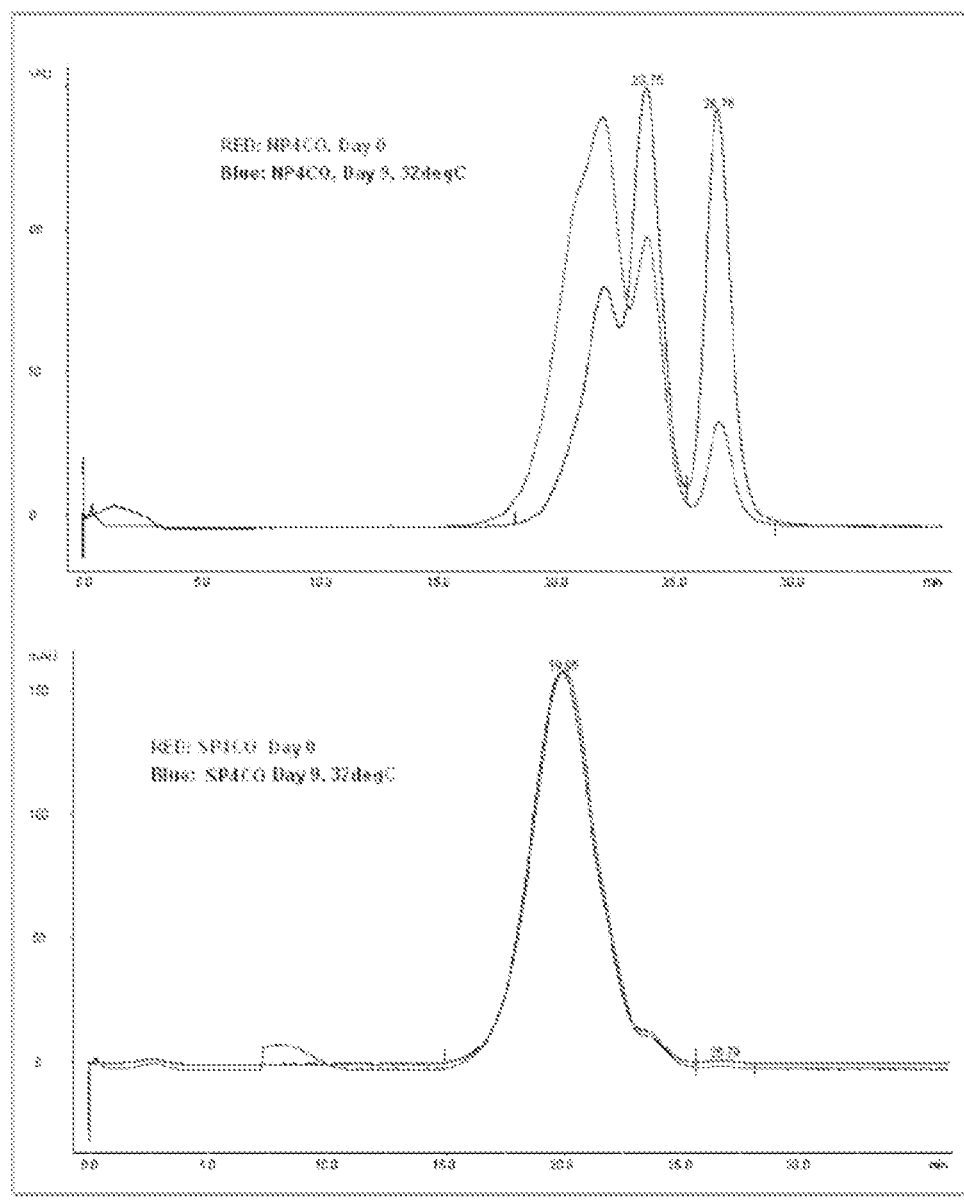
Figure 6: LC under high-salt, dissociating conditions (0.9M $MgCl_2$) analysis of NPC-PEG-Hb (NP4CO, top) versus SVA-PEG-Hb (SP4CO, bottom) at 32°C for 9 days.

POLYALKYLENE OXIDE VALERATE HEMOGLOBIN CONJUGATES

FIELD OF THE INVENTION

The present invention generally relates to polyalkylene oxide (PAO) hemoglobin conjugates. More specifically, the present invention relates to PAO hemoglobin conjugates having improved stability, pharmaceutical compositions containing such conjugates, and methods for synthesizing and using the conjugates.

BACKGROUND OF THE INVENTION

Hemoglobin-based oxygen carriers ("HBOC") have long been associated with vasoconstriction that has been attributed to nitric oxide (NO) scavenging by heme. Oxygen carriers that are useful as oxygen therapeutics (sometimes referred to as "oxygen-carrying plasma expanders"), such as stabilized hemoglobin (Hb), have been shown to have limited efficacy because they scavenge nitric oxide, causing vasoconstriction and hypertension. The propensity of these oxygen carrying solutions to cause vasoconstriction can manifest as hypertension in animals and man. Although the mechanisms underlying the vasoconstrictive effects of HBOCs are not well understood, it has been suggested that the heme iron may combine rapidly and irreversibly with endogenous NO, a powerful vasodilator, thereby causing vasoconstriction.

In part because of these vasoconstrictive effects, no oxygen carrier to date has been entirely successful as an oxygen therapeutic agent (OTA), although products comprising modified cell-free Hb have been the most promising. Human Hb cross-linked between α-chains with bis-dibromosalicyl-fumarate (ααHb) was developed by the U.S. Army as a model red cell substitute, but was abandoned after it exhibited severe increases in pulmonary and systemic vascular resistance (Hess, J. et al., 1991, Blood 78:356A). A commercial version of this product was also abandoned after a disappointing Phase III clinical trial (Winslow, R. M., 2000, Vox Sang 79:1-20).

Two molecular approaches have been advanced in attempting to overcome the NO binding activity of Hb. The first approach used site-directed mutagenesis of the distal heme pocket in an attempt to create a recombinant hemoglobin with reduced NO-binding affinity (Eich, R. F. et al., 1996, Biochem. 35:6976-83). The second approach used a chemical modification approach wherein the size of the Hb was enhanced through oligomerization in an attempt to reduce or possibly completely inhibit the extravasation of Hb from the vascular space into the interstitial space (Hess, J. R. et al., 1978, J. Appl. Physiol. 74:1769-78; Muldoon, S. M. et al., 1996, J. Lab. Clin. Med. 128:579-83; Macdonald, V. W. et al., 1994, Biotechnology 22:565-75; Furchgott, R., 1984, Ann. Rev. Pharmacol. 24:175-97; and Kilbourne, R. et al., 1994, Biochem. Biophys. Res. Commun 199:155-62).

In fact, recombinant Hbs with reduced association binding rates for NO have been produced that are less hypertensive in top-load rat experiments (Doherty, D. H. et al. 1998, Nature Biotechnology 16:672-676 and Lemon, D. D. et al. 1996, Biotech 24:378). However, studies suggest that NO binding may not be the only explanation for the vasoactivity of Hb. It has been found that certain large Hb molecules, such as those modified with polyethylene glycol (PEG), were virtually free of vasoconstriction, even though their NO association rates were identical to those of the severely hypertensive ααHb (Rohlfs, R. J. et al. 1998, J Biol. Chem. 273:12128-12134). Furthermore, it was found that PEG-Hb was extraordinarily effective in preventing the consequences of hemorrhage when given as an exchange transfusion prior to hemorrhage (Winslow, R. M. et al. 1998, J. Appl. Physiol. 85:993-1003).

The conjugation of PEG to Hb reduces its antigenicity and extends its circulation half-life. However, the PEG conjugation reaction has been reported to result in dissociation of Hb tetramers into αβ-dimer subunits causing gross hemoglobinuria in exchange-transfused rats receiving PEG-conjugates of Hb monomeric units below 40,000 Daltons ("Da") (Iwashita and Ajisaka Organ-Directed Toxicity: Chem. Indicies Mech., Proc. Symp., Brown et al. 1981, Eds. Pergamon, Oxford, England pgs 97-101). A polyalkylene oxide ("PAO") conjugated Hb having a molecular weight greater than 84,000 Daltons was prepared by Enzon, Inc. (U.S. Pat. No. 5,650,388) that carried about 10 copies of PEG-5,000 chains linked to Hb at its α and ε-amino groups. This degree of substitution was described as avoiding clinically significant nephrotoxicity associated with hemoglobinuria in mammals. However, the conjugation reaction resulted in a heterogeneous conjugate population and contained other undesirable reactants that had to be removed by column chromatography.

PEG conjugation is typically carried out through the reaction of an activated PEG moiety with a functional group on the surface of biomolecules. The most common functional groups are the amino groups of lysine, imidazole groups of histidine residues, and the N-terminus of proteins; thiol groups of cysteine residues; and the hydroxyl groups of serine, threonine and tyrosine residues and the C-terminus of the protein. PEG is usually activated by converting the hydroxyl terminus to a reactive moiety capable of reacting with these functional groups in a mild aqueous environment. One of the most common monofunctional PEGs used for conjugation of therapeutic biopharmaceuticals is methoxy-PEG ("mPEG-OH"), which has only one functional group (i.e. hydroxyl), thus minimizing cross-linking and aggregation problems that are associated with bifunctional PEG. However, mPEG-OH is often contaminated with high molecular weight bifunctional PEG (i.e. "PEG diol"), which can range as high as 10 to 15% (Dust J. M. et al. 1990, Macromolecule 23:3742-3746) due to its production process. This bifunctional PEG diol has roughly twice the size of the desired monofunctional PEG. The contamination problem is further aggravated as the molecular weight of PEG increases. The purity of mPEG-OH is especially critical for the production of PEGylated biotherapeutics, because the FDA requires a high level of reproducibility in the production processes and quality of the final drug product.

Conjugation of Hb to PAOs has been performed in both the oxygenated and deoxygenated states. U.S. Pat. No. 6,844,317 describes conjugating Hb in the oxygenated, or "R" state by equilibrating Hb with the atmosphere prior to conjugation to enhance the oxygen affinity of the resultant PEG-Hb conjugate. Others describe a deoxygenation step prior to conjugation to diminish the oxygen affinity and increase structural stability, enabling the Hb to withstand the physical stresses of chemical modification, diafiltration and/or sterile filtration and pasteurization (U.S. Pat. No. 5,234,903). For intramolecular cross-linking of Hb, it is suggested that deoxygenating Hb prior to modification may be required to expose lysine 99 of the α-chain to the cross-linking reagent (U.S. Pat. No. 5,234,903).

The kinetics of Hb thiolation with 2-iminothiolane prior to conjugation with PEG was investigated by Acharya et al. (U.S. Pat. No. 7,501,499). It was observed that increasing the concentration of iminothiolane from 10-fold, which introduced an average of five extrinsic thiols per tetramer, to 30-fold nearly doubled the number of extrinsic thiols on Hb. However, the size enhancement seen after PEG conjugation was only marginal, even with double the number of thiols. This suggested that the conjugation reaction in the presence of 20-fold molar excess of maleimidyl PEG-5000 covered the surface of the Hb with less reactive thiols, resulting in steric interference that resisted further modification of Hb with more reactive thiols. Consequently, to achieve the desired degree of conjugation of modified Hb (i.e. 6±1 PEG per Hb molecule), Acharya et al. thiolated Hb with an 8-15 molar excess of iminothiolane, and then reacted the thiolated Hb with a 16-30 fold molar excess of maleimidyl PEG-5000. However, these high molar excess reactant concentrations in large-scale production significantly increase the cost for preparing the HBOC and increase the heterogeneity of the final product. Moreover, such high molar excess of the maleimidyl PEG-5000 also results in a more heterogeneous product with the production of a greater number of unwanted side reactants.

In previous studies, it was observed that the molecular size of surface modified hemoglobin has to be large enough to avoid being cleared by the kidneys and to achieve the desired circulation half-life. Blumenstein, J. et al., determined that this could be achieved at, or above, a molecular weight of 84,000 Daltons ("Da") ("Blood Substitutes and Plasma Expanders," Alan R. Liss, editors, New York, N.Y., pages 205-212 (1978)). In that study, the authors conjugated dextran of varying molecular weight to Hb. They reported that a conjugate of Hb (with a molecular weight of 64,000 Da) and dextran (having a molecular weight of 20,000 Da) "was cleared slowly from the circulation and negligibly through the kidneys." Further, it was observed that increasing the molecular weight above 84,000 Da did not significantly alter these clearance curves. Intramolecular cross-linking chemically binds together subunits of the tetrameric hemoglobin unit to prevent the formation of dimers which are prematurely excreted by the kidney. (See, e.g., U.S. Pat. No. 5,296,465)

In order to bond polyalkylene oxides to hemoglobin, the terminal end-groups of the polymer must first be "activated" (i.e., converted into reactive functional groups) to form an "activated polyalkylene oxide." In the past, PEG-OH was used to prepare PEG-halide, mesylate or tosylate, which was then converted to PEG-amine by performing a nucleophilic displacement reaction with aqueous ammonia (Hoffmann Reaction), sodium azide or potassium phthalimide (Gabriel Reagent). The reaction of PEG-halide with ammonia forms PEG-amine ("PEG-NH$_2$") directly (See Zalipsky et al. Eur. Polym. J. 1983, 19:1177-1183), which could then be used for conjugation to —COOH groups found on some biologically active compounds.

More recently, PEG-NH$_2$ has been used as an intermediate and can be further functionalized to bind groups other than —COOH. For example, PEG-NH$_2$ can be modified to contain a sulfhydryl-activating group such as maleimide. In a reaction disclosed in U.S. Pat. No. 6,828,401, mPEG-maleimide (i.e. methoxy-PEG, or mPEG, to which a maleimide has been added) is prepared by reacting mPEG-OH with p-toluenesulfonyl chloride (a tosylating agent) and triethyleneamine ("TEA", a base catalyst), in dichloromethane (an organic solvent) to produce mPEG-tosylate. This compound is then reacted with 28% aqueous ammonia, which is then reacted with maleic anhydride in a mixture of organic solvents of N, N-dimethylacetamide ("DMAC") and N-cyclohexylpyrrolidinone ("CHP") to produce a maleamic acid compound. This compound is then reacted with pentafluorophenyl trifluoroacetate in the presence of a base catalyst such as diethylaniline ("DEA") or diisopropylethylamine ("DIEA"), in an organic solvent mixture of dichloromethane and dimethyl formamide ("DMF"), to produce the mPEG-maleimide. However, this multi-step, multi-reagent method for obtaining an activated PEG is cumbersome and time consuming.

Disclosed herein is a method for preparing PEG-hemoglobin conjugates by using succinimidyl-valerate activated PEG (SVA-PEG) that binds to amine groups of the hemoglobin under specific conditions to form a stable, homogeneous PEG-hemoglobin conjugate.

SUMMARY OF THE INVENTION

An aspect of the invention is directed to a PAO hemoglobin conjugate having a P50 ranging from about 2 to about 30 mmHg as measured at 37° C. and pH 7.4. The PAO is covalently attached via an amino reactive moiety of an amino acid side chain on the hemoglobin molecule. The amino reactive moiety is linked to the PAO by —C(O)—(CH$_2$)$_p$— wherein p is an integer from 1 to about 20. The hemoglobin is optionally intramolecularly-crosslinked.

Another aspect of the present invention is directed to a PAO hemoglobin conjugate having the structure

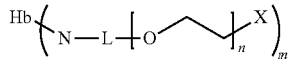

wherein Hb is hemoglobin, L is a linker —C(O)—(CH$_2$)$_p$—, N is an amino group of the hemoglobin, X is a terminal group, m is the average number of activated-PEG polymers conjugated to the hemoglobin, n is the average number of oxyethylene units of a PEG having an average molecular weight of from about 2,000 to about 20,000 Daltons, and p is an integer from 1 to 20.

Yet another aspect of the invention is directed to a PAO hemoglobin conjugate prepared by a process comprising reacting hemoglobin with at least one PAO polymer. The PAO polymer has the structure:

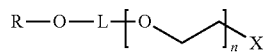

wherein R is the amino reactive moiety, L is a linker —C(O)—(CH$_2$)$_p$—, X is a terminal group, n is the average number of oxyethylene units of a PEG having an average molecular weight of about 2,000 to about 20,000 Daltons, and p is an integer from 1 to 20.

Still another aspect of the invention is directed to a pharmaceutical composition comprising any of the above hemoglobin conjugates and a pharmaceutically acceptable carrier. The compositions can be for use in the treatment of acute liver failure, beta thalassemia, a burn, chronic critical limb ischemia, carbon dioxide or cyanide poisoning, chronic obstructive pulmonary disease (COPD), congestive heart failure, hypoxia, malaria, organ ischemia, peripheral vascular disease, porphyria, pre-eclampsia in pregnancy, sepsis, sickle cell disease, retinal disease, an intra-ocular condition, testicular torsion, trauma, shock, traumatic brain injury, ulcers, vasospasm, or a combination thereof. The compositions can also be for use as an adjunct to angioplasty, as an adjunct for plastic surgery, or as an adjunct in implanting a ventricular assist device; as a blood substitute, a cardioprotectant, a cryopreservative, a hemodialysis adjunct, an oncology agent, an organ preservative, a performance enhancement agent, a surgery adjunct, or a wound healing agent; in imaging; to improve lung function; or a combination thereof. The compositions can also be for veterinary treatment of loss of blood due to injury, hemolytic anemia, infectious anemia, bacterial infection, Factor IV fragmentation, hypersplenation and splenomegaly, hemorrhagic syndrome in poultry, hypoplastic anemia, aplastic anemia, idiopathic immune hemolytic conditions, iron deficiency, isoimmune hemolytic anemia, microangiopathic hemolytic anemia, parasitism, or surgical-anesthesia induced brain damage, or a combination thereof.

Still another aspect of the invention is directed to a method of treatment comprising administering such a hemoglobin conjugate or pharmaceutical composition to a subject in need thereof. The method is for the treatment of any one or more of the conditions described above.

Another aspect of the invention is directed to a method of delivering oxygen, nitric oxide, carbon monoxide or mixtures thereof to tissue and reducing nitrite to nitric oxide (NO) in the microvasculature. The method comprises administering any of the hemoglobin conjugates or the pharmaceutical composition as described above to a subject in need thereof. Following administration, unliganded hemes in the hemoglobin convert nitrite to nitric oxide in the microvasculature.

Yet another aspect of the invention is directed to a method for preparing the hemoglobin conjugate comprising reacting hemoglobin with a PAO polymer having the structure:

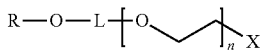

wherein R is the amino reactive moiety, L is a linker —C(O)—(CH$_2$)$_p$—, X is a terminal group, n is the average number of oxyethylene units of a PEG having an average molecular weight of about 2,000 to about 20,000 Daltons, and p is an integer from 1 to 20.

Other objects and features will be in part apparent and in part pointed out hereinafter.

BRIEF DESCRIPTION OF THE DRAWINGS

FIG. 1 depicts a flow chart of an exemplary method for preparing amine PEGylated Hemoglobin using methoxy PEG Succinimidyl Valerate (mPEG-SVA) as a starting material, wherein R$_1$, R$_2$ and R$_3$ are portions of the hemoglobin main chain.

FIG. 2 depicts the chemical structures and bond lengths for (1) p-nitrophenyl carbonate-PEG (NPC-PEG), (2) succinimidylcarbonate-PEG (SC-PEG), (3) maleimide-PEG (Mal-PEG), and (4) Succinimidyl Valerate-PEG (SVA-PEG) wherein arrows show the distance of the PEG backbone from the active group.

FIG. 3 depicts the distance between the linkage with hemoglobin and the PEG backbone for Mal-PEG (top), SVA-PEG (middle) and SC-PEG (bottom).

FIG. 4 is a size-exclusion chromatogram (LC) under non-dissociating conditions of SVA-PEG-Hb (blue) as compared to MP4 (red) and stroma-free hemoglobin (SFH) (green).

FIG. 5 is a size-exclusion chromatogram (LC) under high-salt, dissociating conditions (0.9M MgCl$_2$) of SVA-PEG-Hb (SP4CO, bottom) as compared to MP4CO (top) under accelerated storage conditions at 40° C. for up to one month.

FIG. 6 is an LC under high-salt, dissociating conditions of SVA-PEG-Hb (SP4CO, bottom) as compared to NPC-PEG-Hb (NP4CO, top) under accelerated storage conditions at 32° C. for 9 days.

Corresponding reference characters indicate corresponding parts throughout the drawings.

DESCRIPTION OF THE PREFERRED EMBODIMENTS

The polyalkylene oxide hemoglobin conjugates of the invention, and the pharmaceutical compositions thereof, exhibit enhanced stability as compared to known oxygen or non-oxygenated hemoglobin therapeutics with respect to long and short-term storage stability against the formation of higher molecular weight constituents observed by LC under dissociating conditions or against separation of PAO from the hemoglobin. They are also more homogeneous than known oxygen or non-oxygenated hemoglobin therapeutics. These conjugates can also be made via a simple, one-step reaction under mild conditions with a short reaction time as compared to reaction times required to make known hemoglobin therapeutics.

Without being bound to any particular theory, it is believed that the valerate linker between the hemoglobin and the PAO causes the enhanced stability. The distance between the PAO and the linkage to the hemoglobin molecule as a result of the valerate linker is greater than that of other common linkers such as p-nitrophenyl carbonate-PEG (NPC-PEG), succinimidylcarbonate-PEG (SC-PEG), and maleimide-PEG (MalPEG). This greater spacing of about 8.8 Angstroms from the hemoglobin linkage to the PAO appears to stabilize the PAO-hemoglobin bond.

The present invention is directed to a PAO hemoglobin conjugate having a P50 ranging from about 2 to about 30 mmHg as measured at 37° C. and pH 7.4. The PAO is covalently attached via an amino reactive moiety to an amino acid side chain on the hemoglobin molecule. The amino reactive moiety is linked to the PAO by —C(O)—(CH$_2$)$_p$— wherein p is an integer from 1 to about 20, preferably from 1 to about 12, more preferably from 1 to about 8, from 2 to about 6, and most preferably p is 4.

The hemoglobin is optionally intramolecularly-crosslinked. More specifically, the hemoglobin can be β,β-intramolecularly-crosslinked or α,α-intramolecularly-crosslinked by conventional methods known in the art.

When the hemoglobin is β,β-intramolecularly-crosslinked, the P50 of the PAO hemoglobin conjugate is preferably about 2 to 15 mm Hg, more preferably about 2 to 10 mm Hg, and most preferably about 7 mm Hg.

When the hemoglobin is α,α-intramolecularly-crosslinked, the P50 of the PAO hemoglobin conjugate is preferably from about 20 to 30 mm Hg.

More specifically, the PAO hemoglobin conjugate has the structure:

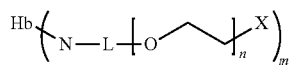

wherein Hb is hemoglobin, N is an amino group of the hemoglobin, L is a linker —C(O)—(CH$_2$)$_p$—, X is a terminal group, m is the average number of activated-PEG polymers conjugated to the hemoglobin, n is the average number of oxyethylene units of a PEG having an average molecular weight of from about 2,000 to about 20,000 Daltons, and p is an integer from 1 to 20. Preferably, the average molecular weight is from about 3,000 to about 10,000 Daltons, more preferably from about 4,000 to about 6,000 Daltons, and most preferably about 5,000 Daltons. Preferably, m, the number of activated-PEG polymers conjugated to the hemoglobin, ranges on average from about 6 to about 10 per hemoglobin tetramer, and is preferably about 7 or 8. The number of ethylene units p in the linker —C(O)—(CH$_2$)$_p$— is preferably an integer from 1 to about 12, more preferably from 1 to about 8, from 2 to about 6, and most preferably p is 4. A preferred PAO hemoglobin conjugate has the structure:

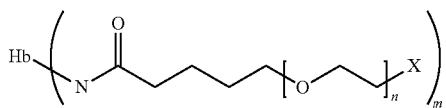

wherein Hb, N, X, m, and n are as defined above.

A PAO hemoglobin conjugate of the invention can be prepared by a process comprising reacting hemoglobin with at least one PAO polymer. The PAO polymer has the structure:

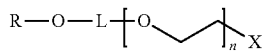

wherein R is the amino reactive moiety, L is a linker —C(O)—(CH$_2$)$_p$—, X is a terminal group, n is the average number of oxyethylene units of a PEG having an average molecular weight of about 2,000 to about 20,000 Daltons, and p is an integer from 1 to 20. Preferably, the average molecular weight is about 3,000 to about 10,000 Daltons, more preferably from about 4,000 to about 6,000 Daltons, and most preferably about 5,000 Daltons. The number of ethylene units p in the linker —C(O)—(CH$_2$)$_p$— is preferably an integer from 1 to about 12, more preferably from 1 to about 8, from 2 to about 6, and most preferably p is 4. The preferred PAO polymer has the structure:

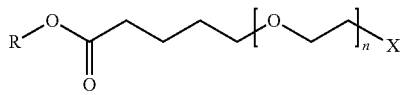

wherein R, X, and n are as defined above.

X is a terminal group of the PAO, and can be hydroxy, aryloxy such as benzyloxy, or $C_1$-$C_{20}$ alkoxy, more preferably $C_1$-$C_{10}$ alkoxy group, and still more preferably a $C_1$-$C_5$ alkoxy group such as methoxy or ethoxy. Preferably, X is methoxy.

R can be any amino reactive moiety that will react with an amino residue of the hemoglobin, such as succinimidyl or p-nitrophenyl. Preferably, R is succinimidyl.

A variety of Hbs may be utilized with the present invention. The Hb may be obtained from animal sources, such as human, bovine, porcine, or equine hemoglobin. Human Hb is preferred. The Hb can be obtained from natural sources or can be recombinant (e.g., as produced by known recombinant methods).

The hemoglobins of the present invention can have a high oxygen affinity ranging from about 2 to about 20 mmHg, preferably from about 2 to about 10 mmHg, and more preferably 7 mmHg.

The hemoglobins can be intramolecularly crosslinked to prevent dissociation into dimers and to avoid being cleared by the kidneys, extending circulation half-life. A variety of methods are known in the art for intramolecularly crosslinking Hb. Chemical crosslinking reagents include glutaraldehyde (U.S. Pat. No. 7,005,414), polyaldehydes (U.S. Pat. No. 4,857,636), diaspirin (U.S. Pat. No. 4,529,719), pyridoxyl-5'-phosphate (U.S. Pat. No. 4,529,719) trimesoyltris (methyl phosphate) (U.S. Pat. No. 5,250,665), dialkynes (for reaction with hemoglobin having an azide linker. See Foot et al., Chem. Commun. 2009, 7315-7317; Yang et al., Chem. Commun. 2010, 46: 7557-7559) and hemoglobins can be crosslinked via recombinant methodologies.

B,β-DBBF crosslinked Hb can be prepared by reaction of stroma-free hemoglobin prepared from packed red blood cells with bis(3,5-dibromosalicyl)fumarate (DBBF) as described previously by Walder, Biochem, 1979: Vol 18 (20): 4265-70. For example, oxygenated SFH in borate buffer (pH~8.5) can be reacted with two-fold molar excess of DBBF for about 16 hours at about 2-8° C.

Polyethylene oxides for use in conjugating hemoglobins of the invention include, but are not limited to, polyethylene oxide, polypropylene oxide and a polyethylene/polypropylene oxide copolymer. The PAO has a molecular weight of about 2,000 to about 20,000 Daltons, preferably from about 3,000 to about 10,000 Daltons, more preferably from 4,000 to about 6,000 Daltons, and most preferably about 5,000 Daltons. The most common PAO presently used to modify the surface of Hb is PEG because of its pharmaceutical acceptability and commercial availability. PEG is available in a variety of molecular weights based on the number of repeating subunits of ethylene oxide (i.e. —CH$_2$CH$_2$O—) within the molecule, to achieve a desired molecular weight based on the number and size of the PEG molecules conjugated to Hb.

One or both of the terminal end groups of the PAO polymer are converted into a reactive functional group ("activated"). For example, PEG-OH has been used to prepare PEG-halide, mesylate or tosylate, which is then converted to PEG-amine ("PEG-NH$_2$") by performing a nucleophilic displacement reaction with aqueous ammonia (Zalipsky, S. et al., 1983, Eur. Polym. J. 19:1177-1183), sodium azide or potassium phthalimide. The activated PEG can then be conjugated to a heme protein through the interaction of the PEG amine group (—"NH$_2$") with a carboxyl group ("—COOH") of the heme protein.

A number of molecules containing functional groups are available commercially to permit the modification of proteins by the addition of other molecules. These molecules, such as polyethylene glycol, are usually activated at their termini by adding one or more functional groups thereto. As used herein, the PAO is activated by modifying it to contain a succinimidyl group, or "succinimide". A succinimide is a cyclic imide with the formula $C_4H_5NO_2$, which is reactive with the free amines in lysines and terminal valines within the sequence of the protein. In comparison, a maleimide is a cyclic unsaturated imide of the formula $H_2C_2(CO)_2NH$, which is reactive with the free sulfhydryls in cysteine residues and can also react with free amines in lysine and histidine residues to a lesser extent. The succinimides form a stable leaving group from an active ester of valerate, whereas the maleimides react directly with a sulfhydryl group to form a covalent bond.

The activated PAO includes a spacer linking an amine reactive moiety to the PAO. The spacer is preferably a divalent valerate ion. Such activated PAOs are commercially available and include, for example, methoxypoly(ethylene glycol) succinimidyl valerate (mPEG-SVA) ((Laysan Bio, Inc., Arab, Ala.). Such functional PEG can be conjugated to the surface amino acid side chains such as lysine residues or the terminal valine residue of hemoglobin using known methods.

Non-limiting examples of amino acid residue side chains of human Hb that can be modified using amine reactive chemistry for conjugation to PAO are presented in Table 1 below:

TABLE 1

Amine Reactive Chemistry and Potential Sites of Modification

| Residues | Positions | Reacts With |
| --- | --- | --- |
| α-chain | | |
| Lys | 7, 11, 16, 40, 56, 60, 61, 90, 99, 127 and 139 | Succinimide; NPC (p-nitrophenyl carbonate); isocyanate; aldehyde; isothiocyanate; epoxides. |
| His | 20, 45, 50, 58, 72, 87, 112 and 122 | Succinimide; NPC (p-nitrophenyl carbonate); isocyanate; aldehyde; isothiocyanate; epoxides. |
| Val | 1 | Succinimide; NPC (p-nitrophenyl carbonate); isocyanate; aldehyde; isothiocyanate; epoxides. |
| β-chain | | |
| Lys | 8, 17, 59, 61, 65, 66, 82, 95, 120, 132 and 144 | Succinimide; NPC (p-nitrophenyl carbonate); isocyanate; aldehyde; isothiocyanate; epoxides. |
| His | 2, 63, 77, 92, 97, 116, 117, 143 and 146 | Succinimide; NPC (p-nitrophenyl carbonate); isocyanate; aldehyde; isothiocyanate; epoxides. |
| Val | 1 | Succinimide; NPC (p-nitrophenyl carbonate); isocyanate; aldehyde; isothiocyanate; epoxides. |

The molecular weight of the PAO-Hb can be regulated by the conjugation reaction. Increasing the molar ratios of the reactants for the conjugation process generally increases the number of PEG molecules bound to Hb. Preferably, from about 8-fold to about 20-fold molar excess of the activated PAO over Hb is used in the conjugation reaction. More preferably, a 10-fold molar excess of the activated PAO such as mPEG-SVA over Hb is used.

Hemoglobin is conjugated with the activated polyalkylene oxide when hemoglobin is in its oxygenated state to increase the oxygen affinity of the Hb-PAO conjugate.

Hemoglobin can also be conjugated with the activated polyalkylene oxide when it is in the deoxygenated state to lower oxygen affinity relative to that conjugated in the oxygenated state.

SVA-PEGylated hemoglobin can be prepared using a one-step mPEG-SVA conjugation reaction, with relatively short reaction times. In one embodiment, the starting materials, mPEG-SVA and hemoglobin, are reacted for about 1 to about 2 hours at a pH of about 7 to about 8.5, at a temperature of about 5 to about 15° C. The PAO polymer is present at a concentration of between about 8-fold and about 20-fold molar excess over the hemoglobin concentration, preferably 10-fold.

When compared to PEGylation of hemoglobin using mPEG-Mal, the following advantages are achieved: 1) there is no need for a separate thiolation reaction to increase the number of sites of reaction of the mPEG-Mal with hemoglobin; 2) the resultant conjugate is more homogeneous, which is believed to result from the amide linkage being more stable and/or lack of impurities from residual iminothiolane; 3) the reaction is more efficient, thus reducing reaction time; 4) the native (393 cysteine moieties in the hemoglobin are preserved, which in turn enhances heme stability; 5) and the valerate linkage is more stable, which is believed to result from the increase in the distance between the succinimide group and the PEG polymer from 3.5 Angstroms to 8.8 Angströms.

The hemoglobin conjugates of the invention can be in oxygenated or deoxygenated form, can be liganded to CO or NO, or can be a mixture including two or more of these four forms. $HbO_2$ is prepared by equilibrating non-oxygenated hemoglobin with air, pure $O_2$ gas or $O_2$/nitrogen gas mixtures.

Deoxygenation can be performed by any method known in the art. One simple method is to expose the hemoglobin solution to an inert gas, such as nitrogen, argon or helium. To assure that deoxygenation is relatively homogeneous, the Hb solution is circulated in this process. Monitoring deoxygenation to attain desired levels may be performed by using a Co-oximeter 682 (Instrument Laboratories). If partial reoxygenation is desired, deoxygenated Hb may be exposed to oxygen or to a gas mixture containing oxygen, such as air.

Gas exchange to replace molecular oxygen with another gas may be accomplished through a gas-permeable membrane, such as a polypropylene or cellulose acetate membrane. See, for example, published U.S. Patent Application No. 2006/0234915. Commercially available gas-exchange devices utilizing these membranes include the Celgard™ polypropylene microporous hollow fiber device from Hoechst-Celanese (Dallas, Tex.) or the Cell-Pharm™ hollow fiber oxygenator from American Laboratory (East Lyme, Conn.). In the Hoechst-Celanese Celgard™ device, oxygenated Hb is deoxygenated by passing an aqueous Hb solution through polypropylene microporous hollow filters at 10-100 ml/min/ft² while the system is purged with nitrogen at 5-20 psi. The Hb is generally circulated for about 5 to 30 minutes to achieve the desired percentage of deoxyHb. Another method for producing deoxygenated Hb comprises exposing a Hb solution to a chemical reducing agent such as sodium ascorbate, sodium dithionate and sodium bisulfate. Hb is partially deoxygenated by adjusting the reducing agent concentration, reaction time and temperature. Alternatively, a reducing agent may be used to substantially deoxygenate Hb, and then oxygen may be reintroduced to form a partially deoxygenated product. For example, Hb can be exposed to a 100 mM concentration of sodium bisulfite for about one hour before adding antioxidants.

Hb can be liganded to CO using any known methods for forming oxyhemoglobin, simply by substituting CO for $O_2$. This generally involves introducing a source of CO to a solution of hemoglobin such that the hemoglobin becomes liganded with CO instead of $O_2$ (K. D. Vandegriff, et al., Biochem. J. 382:183-189 (2004)). Since hemoglobin has a higher affinity for CO than it does for oxygen, it is not necessary to first deoxygenate the hemoglobin. Accordingly, the most convenient way of forming CO-Hb complexes is by introducing 100% gaseous CO to a solution of hemoglobin.

HbNO can be prepared by reacting deoxygenated hemoglobin with nitric oxide gas, or by exposing CO-Hb to NO gas such that the NO exchanges for CO. HbNO can also be made by reacting deoxygenated hemoglobin with a small NO-donor molecule like PROLI NONOate™ (i.e., 1-(hydroxy-NNO-azoxy)-L-proline, disodium salt; Cayman Chemical, Ann Arbor, Mich.).

It should be noted that hemoglobin to which NO, a free radical, is bound to the amino acid side groups in the globin chain are not NO-Hb complexes as defined herein, since such compounds do not contain diatomic (nonionic) NO as a ligand in the heme pocket instead of oxygen. For example, nitrosylhemoglobin is formed when native hemoglobin is exposed to a NO donor under conditions that cause it to bind to free sulfhydryl groups (U.S. Pat. No. 6,627,738). Such nitrosylhemoglobins still carry oxygen, whereas the NO-Hb complexes of the present invention do not. Furthermore, when the modified hemoglobin is formed by a reaction directed towards sulfhydryl moieties such as described above, these moieties are no longer available for NO binding.

The PAO-Hb conjugates of the present invention can be formulated as a pharmaceutical composition comprising the PAO-Hb conjugate in a pharmaceutically acceptable carrier for parenteral administration, such as an aqueous diluent. The concentration of the PAO-Hb conjugate in the carrier can vary according to the application. Preferably, the PAO-Hb conjugate concentration ranges from about 0.1 g/dl to about 10 g/dl, more preferably from about 2.0 g/dl to about 8.0 g/dl, and most preferably about 4.0 to about 6.0 g/dl. The selection of an appropriate concentration of hemoglobin depends on the colloidal osmotic (oncotic) properties of the final hemoglobin product. Preferably, the compositions of the invention are normo-oncotic as compared to whole blood or hyperoncotic as compared to plasma. The hemoglobin concentration can be adjusted to obtain the desired oncotic pressure for each indication.

When the composition is formulated as a parenteral, the solution generally comprises a physiologically compatible electrolyte carrier isosmotic with whole blood and which maintains the reversible oxygen-, CO- or NO-carrying and delivery properties of the hemoglobin.

The pharmaceutically acceptable carrier can be an aqueous diluent. The aqueous diluent can comprise an aqueous solution of a colloid or an aqueous solution of a non-oxygen carrying component, such as an aqueous solution of proteins such as albumin, an aqueous solution of glycoproteins, an aqueous solution of polysaccharides, or a combination thereof. The aqueous diluent can comprise an aqueous cell-free solution.

Suitable aqueous diluents include, but are not limited to, physiological saline, a saline-glucose mixture, Ringer's solution, lactated Ringer's solution, Locke-Ringer's solution, Krebs-Ringer's solution, Hartmann's balanced saline, heparinized sodium citrate-citric acid-dextrose solution, an acetate solution, a multiple electrolyte solution (e.g., Plasma Lyte® or Plasma Lyte-A® from Baxter International, Deerfield, Ill.), a lactobionate solution, and polymeric plasma substitutes, such as polyethylene oxide, polyvinyl pyrrolidone, polyvinyl alcohol, an ethylene oxide-propylene glycol condensate, or a combination thereof.

The composition can additionally comprise pharmaceutically-acceptable fillers, salts, and other materials well-known in the art, the selection of which depends on the dosage form, the condition being treated, the particular purpose to be achieved according to the determination of the ordinarily skilled artisan in the field and the properties of such additives. For example, the composition can include physiological buffers, carbohydrates (e.g. glucose, mannitol, or sorbitol), alcohols or poly alcohols, pharmaceutically acceptable salts (e.g., sodium or potassium chloride), surfactants (e.g., polysorbate 80), anti-oxidants, anti-bacterial agents, oncotic pressure agents (e.g. albumin or polyethylene glycols) or reducing agents (e.g., ascorbic acid, glutathione, or N-acetyl cysteine).

The pharmaceutical compositions have a viscosity of at least about 2 centipoise (cP). More specifically, the viscosity ranges from about 2 to about 5 cP, and particularly about 2.5 to about 4.5 cP.

In order to avoid complications in administration, the pharmaceutical composition is of high purity, i.e. free from stroma, phospholipids, and pyrogens, having an endotoxin level of no more than 0.25 EU/ml, as measured by the LAL (limulus amebocyte lysate) test, and having less than 8% methemoglobin.

Pharmaceutical compositions can be administered parenterally, such as by subcutaneous, intravenous, or intramuscular injection, or as large volume parenteral solutions. The compositions can also be administered by gavage.

A typical dose of hemoglobin conjugate as a therapeutic agent can be from about 1 to about 15,000 milligrams of hemoglobin per kilogram of patient body weight. For example, when used as an oxygen therapeutic, the dosage will range between 100 to 7500 mg/kg patient body weight, more preferably 500 to 5000 mg/kg body weight, and most preferably 700 to 3000 mg/kg body weight. Thus, a typical dose for a human patient might be from a gram to over 1000 grams. It will be appreciated that the unit content of active ingredients contained in an individual dose of each dosage form need not in itself constitute an effective amount, as the necessary effective amount could be reached by administration of a number of individual doses. The selection of dosage depends upon the dosage form utilized, the condition being treated, and the particular purpose to be achieved according to the determination of those skilled in the art.

The PAO-Hb conjugates and pharmaceutical compositions can be used to deliver oxygen, CO and/or NO to a subject. A method of delivering oxygen, nitric oxide, carbon monoxide or mixtures thereof to tissue and reducing nitrite to produce further endogenous nitric oxide (NO) in the microvasculature includes administering the hemoglobin conjugate or the composition to a subject in need thereof, wherein following administration, the hemoglobin becomes unliganded and converts nitrite to nitric oxide in the microvasculature.

The hemoglobin conjugates and compositions thereof of the invention can be used: to treat acute liver failure, beta thalassemia, a burn, chronic critical limb ischemia, carbon dioxide or cyanide poisoning, chronic obstructive pulmonary disease (COPD) (e.g., acute exacerbations), congestive heart failure (e.g., acute heart failure, chronic heart failure), hypoxia (e.g., high altitude use including for pulmonary edema, decompression sickness), malaria (e.g., cerebral malaria (Falciparum occlusive events), organ ischemia (e.g., acute bowel ischemia (torsion), acute bowel ischemia (embolism), cardiogenic shock, acute vascular organ ischemia, stroke (before CAT scan), stroke (after CAT scan), myocardial infarction/severe cardiac ischemia), peripheral vascular disease, porphyria, pre-eclampsia in pregnancy, sepsis, sickle cell disease (e.g., stroke/transient ischemic attack, splenic sequestration, hepatic sequestration, priapism), retinal disease/intra-ocular condition (e.g., central retinal artery occlusion, central venous occlusion), testicular torsion, trauma/shock (e.g., traumatic hemorrhagic shock, non-traumatic hemorrhagic shock, pre-hospital/field use (military/emergency), traumatic brain injury/blast), ulcers, or vasospasm; as an adjunct to angioplasty, as an adjunct for plastic surgery (skin flaps) (e.g., acute treatment, chronic treatment), or as an adjunct in implanting a ventricular assist device; as a blood substitute (e.g., for acute blood loss, Jehovah's Witness, difficult to cross-match patient, rare blood group, sickle aplastic crisis, sickle cell anemia perioperative management, acute hemolytic anemia (autoimmune), acute hemolytic anemia (toxin), or other refractory anemia), a cardioprotectant, a cryopreservative, a hemodialysis adjunct, an oncology agent (e.g., adjunct to radiotherapy or chemotherapy, solid tumors), an organ preservative (e.g., ex vivo, in donor, in recipient), a performance enhancement agent (e.g., civilian/athletic, military), a surgery adjunct (e.g., cardiopulmonary bypass (prime), cardiopulmonary bypass (adjustment), lung ischemia, pre-surgery conditioning, ruptured aortic aneurysm, replacement of thoracic aorta (dissection or aneurysm)), or a wound healing agent; in imaging (x-ray or magnetic resonance imaging (MRI)); to improve lung function (e.g., acute lung injury, chronic lung injury, transient viral pneumonia, neonatal distress syndrome); or a combination thereof. Such uses include administration of the conjugate or composition to a subject in need thereof.

Further, the hemoglobins and compositions of the invention can be used to treat non-traumatic hemorrhagic shock, pre-hospital setting trauma, traumatic hemorrhagic shock, acute lung injury, adult respiratory distress syndrome, traumatic brain injury, stroke, solid tumor cancer, organ degradation (ex-vivo), organ degradation (in recipient), severe sepsis/septic shock, myocardial infarction/cardiac ischemia, cardiogenic shock, acute heart failure, pulmonary embolism, various conditions by surgery (e.g., adjunct to angioplasty, adjunct to thoracic aortic repairs, adjunct to cardiopulmonary bypass, priming solution for cardiopulmonary bypass), or a combination thereof.

The numerous clinical settings in which the hemoglobins and compositions of the present invention are useful include the following:

Trauma.

An acute loss of whole blood can result in a fluid shift from the interstitial and intracellular spaces to replace the lost volume of blood while shunting of blood away from the low priority organs including the skin and gut. Shunting of blood away from organs reduces and sometimes eliminates $O_2$ levels in these organs and results in progressive tissue death. The primary goal is to oxygenate affected tissues. This trauma can be in a pre-hospital setting or can result in traumatic hemorrhagic shock or traumatic brain injury.

Ischemia.

The conjugates and compositions thereof can also be used to deliver oxygen, CO, and/or NO to areas that red blood cells or many other oxygen therapeutics cannot penetrate. These areas can include any tissue areas that are located downstream of obstructions to red blood cell flow, such as areas downstream of thrombi, sickle cell occlusions, arterial occlusions, angioplasty balloons, surgical instrumentation, and any tissues that are suffering from oxygen starvation or are hypoxic. All types of tissue ischemia can be treated including, for example, stroke, emerging stroke, transient ischemic attacks, myocardial stunning and hibernation, acute or unstable angina, emerging angina, infarct, and the like. In particular, conditions resulting in ischemia include acute heart failure, cardiogenic shock, myocardial infarction/cardiac ischemia, stroke, pulmonary embolism, non-traumatic hemorrhagic shock, or cerebrovascular trauma.

Hemodilution.

In this application, the therapeutic is administered to replace (or substitute for) the $O_2$ levels of the removed autologous blood. This permits the use of the removed autologous blood for necessary transfusions during and after surgery. One such surgery requiring pre-operative blood removal would be a cardiopulmonary bypass procedure.

Sepsis/Septic Shock.

In sepsis, some patients may become hypertensive in spite of massive fluid therapy and treatment with vasoconstrictor agents. In this instance, the overproduction of nitric oxide (NO) results in lowered blood pressure. Therefore hemoglobin is a desirable agent for treatment of these patients because hemoglobin binds NO with a high avidity.

Hypoxemia.

When a patient has acute lung injury caused by either pneumonia or pancreatitis, hypoxemia can be observed and can be alleviated by providing the hemoglobins or compositions of the invention to oxygenate the affected tissues.

Cancer.

Delivery of $O_2$ to the hypoxic inner core of a solid tumor mass increases its sensitivity to radiotherapy and chemotherapy. Because the microvasculature of a tumor is unlike that of other tissues, sensitization through increasing $O_2$ levels requires $O_2$ be unloaded within the hypoxic core. In other words, the P50 should be very low to prevent early unloading of the $O_2$, increasing the $O_2$ levels, to insure optimal sensitization of the tumor to subsequent radiation and chemotherapy treatments.

Surgery.

The hemoglobins and compositions of the invention can be used during various surgical procedures. For example, they can be used as an adjunct to angioplasty, thoracic aortic repairs, during a cardiopulmonary bypass procedure or as a cardiopulmonary priming solution.

Organ Perfusion.

During the time an organ is maintained ex vivo or in an organ donation recipient, maintaining $O_2$ content helps preserve structural and cellular integrity and minimizes infarct formation. The hemoglobins and compositions can sustain the oxygen requirements for such an organ.

The hemoglobins and compositions thereof can also be used in non-humans, such as domestic animals (e.g., livestock and companion animals such as dogs, cats, horses, birds, reptiles. It is contemplated that the present invention finds utility in the emergency treatment of domestic and wild animals suffering a loss of blood due to injury, hemolytic anemias, etc. Veterinary uses include treatment of loss of blood due to injury, hemolytic anemia, infectious anemia, bacterial infection, Factor IV fragmentation, hypersplenation and splenomegaly, hemorrhagic syndrome in poultry, hypoplastic anemia, aplastic anemia, idiopathic immune hemolytic conditions, iron deficiency, isoimmune hemolytic anemia, microangiopathic hemolytic anemia, parasitism, or surgical-anesthesia induced brain damage.

Definitions

When the terms "one," "a" or "an" are used in this disclosure, they mean "at least one" or "one or more," unless otherwise indicated.

"Activated polyalkylene oxide" or "activated PAO" as used herein refer to a PAO molecule that has at least one functional group. A functional group is a reactive moiety that interacts with free amines, sulfhydryls or carboxyl groups on a molecule to be conjugated with PAO. For example, one such functional group that reacts with free sulfhydryls is a maleimide group. A functional group that reacts with free amines is a succinimide group.

"Deoxyhemoglobin" or "unliganded hemoglobin" means any hemoglobin to which no exogenous ligand is bound to heme.

"Hemoglobin" or "Hb" refers generally to a heme protein that transports oxygen. In humans, each molecule of Hb has 4 subunits, 2 α-chain subunits and 2 β-chain subunits, which are arranged in a tetrameric structure. Each subunit also contains one heme group, which is the iron-containing center that in the ferrous ($Fe^{2+}$) binds the ligands $O_2$, NO or CO. Thus, each Hb molecule can bind up to 4 ligand molecules, making $HbO_2$, HbNO, or HbCO liganded compounds, respectively. Additionally, the hemoglobin may be liganded with mixtures of $O_2$, NO and CO.

"Hemoglobin based oxygen carriers" (HBOCs) refers to hemoglobins that carry oxygen, but are also useful for carrying other molecular gases, such as carbon monoxide and nitric oxide.

"High oxygen affinity" refers to hemoglobin that has been modified to exhibit an oxygen affinity greater than that of stroma free-hemoglobin (SFH). Thus, a "high oxygen affinity" Hb has a P50 less than that of SFH, which has a P50 of 15 mmHg as measured at 37° C. and pH 7.4.

"Liganded hemoglobin" means hemoglobin to which an exogenous ligand is bound to heme. Common preferred ligands include oxygen, carbon monoxide, and nitric oxide.

"MalPEG" refers to maleimidyl polyethylene glycol, and includes a maleimidyl moiety attached to polyethylene glycol via a linker.

"MalPEG-Hb" refers to Hb to which maleimidyl-activated PEG has been conjugated. The conjugation is performed by reacting MalPEG with thiol groups (and to a lesser extent, amino groups) on the Hb to form MalPEG-Hb. Thiol groups are found in cysteine residues present in the amino acid sequence of Hb, such as the two intrinsic thiols at βCys 93, and can also be introduced by modifying surface amino groups to contain a thiol group. An exemplary MalPEG-Hb known as MP4 (Sangart, Inc.) has the following formula:

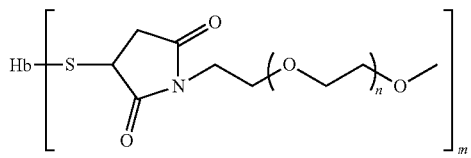

wherein Hb is hemoglobin; S is a thiol group on the hemoglobin; n is the number of oxyethylene units of the 5,000-Dalton polyalkylene oxide polymer; and m is the average number of maleimidyl-activated polyalkylene oxide polymers conjugated to the hemoglobin and is 7-8.

"Methemoglobin" or "metHb" refer to an oxidized form of Hb that contains iron in the ferric state. MetHb does not function as an oxygen or CO carrier. The term "methemoglobin %" as used herein refers to the percentage of oxidized Hb to total Hb.

"Methoxy-PEG" or "mPEG-OH" refer to PEG wherein the hydrogen of the hydroxyl terminus is replaced with a methyl (—$CH_3$) group.

"Modified hemoglobin" or "modified Hb" refers to Hb that has been altered by a chemical reaction, such as intra- and inter-molecular crosslinking, polymerization, conjugation, and/or recombinant techniques, such that the Hb is no longer in its "native" state. As used herein, the terms "hemoglobin" or "Hb" refer to both native unmodified Hb and modified Hb, unless otherwise indicated.

"Nitrite reductase activity" or "NRA" is the ability of hemoglobin or a hemoglobin-based protein to reduce nitrite to nitric oxide. "Maximal nitrite reductase activity" is the maximum rate that hemoglobin or a hemoglobin-based protein is able to reduce nitrite to nitric oxide. "Initial nitrite reductase activity" is the initial rate that hemoglobin or a hemoglobin-based protein reduces nitrite to nitric oxide when nitrite is added to the fully deoxygenated protein.

The term "non-oxygenated" means that the heme protein or hemoglobin is in the non-liganded, deoxygenated state, or it is liganded with a gas other than $O_2$, such as NO or CO.

"Oxygen affinity" refers to the avidity with which an oxygen carrier, such as Hb, binds molecular oxygen. This characteristic is defined by the oxygen equilibrium curve, which relates the degree of saturation of Hb molecules with oxygen (Y axis) with the partial pressure of oxygen (X axis). The position of this curve is denoted by the "$P_{50}$" value, which is the partial pressure of oxygen at which the oxygen carrier is half-saturated with oxygen, and is inversely related to oxygen affinity. Hence, the lower the $P_{50}$, the higher the oxygen affinity. The oxygen affinity of whole blood (and components of whole blood, such as red blood cells and Hb) can be measured by a variety of methods known in the art. (see, e.g., Winslow, R. M. et al., J. Biol. Chem. 1977, 252:2331-37). Oxygen affinity may also be determined using a commercially available HEMOX™ Analyzer (TCS Scientific Corporation, New Hope, Pa.). (see, e.g., Vandegriff and Shrager in "Methods in Enzymology" (Everse et al., eds.) 232:460 (1994)); and Vandegriff, et al., Anal. Biochem. 256(1): 107-116 (1998)).

The term "oxygen therapeutic agent" as used herein refers to a heme protein that is capable of binding to and carrying molecular oxygen to cells/tissues/organs in need thereof. When administered in the form of a CO- or NO-liganded heme protein, once the CO or NO is released from the heme moiety, the heme groups are then free to bind to and carry molecular oxygen.

"Polyethylene glycol" or "PEG" refer to a polymer of the general chemical formula $H(OCH_2CH_2)_nOH$ where "n" is greater than or equal to 4, preferably about 45 to about 500, more preferably about 70 to about 250, and most preferably about 90 to about 140, or about 115. The polymer can be substituted or unsubstituted, and the terminal hydroxy group can be replaced with a different conventional terminal group, such as methoxy or carboxy. PEGs are commercially available from many sources (e.g., Carbowax™ (Dow Chemical, Midland, Mich.), Poly-G® (Arch Chemicals, Norwalk, Conn.) and Solbase).

"Polyethylene glycol-conjugated hemoglobin," "PEG-Hb conjugate" or "PEG-Hb" refer to Hb to which at least one PEG is covalently attached.

"Solution" refers to a liquid mixture and the term "aqueous solution" refers to a solution that contains some water and may also contain one or more other liquid substances with water to form a multi-component solution.

"Stroma-free hemoglobin" or "SFH" refer to Hb from which red blood cell membranes have been removed.

"Surface-modified hemoglobin" refers to hemoglobin to which chemical groups, usually polymers, have been attached, such as dextran or polyalkylene oxide. The term "surface-modified oxygenated hemoglobin" refers to Hb that is in the "R" state when it is surface modified.

"Terminal activity" is an indication of the percentage of PAO that is functionalized with a moiety capable of reacting with a reactive group of the heme protein or hemoglobin. "100% Terminal activity" indicates that the molar excess of the PAO used in the conjugation reaction is expressed on a basis that all of the PAO has a moiety capable of reacting with a reactive group of the heme protein or hemoglobin. For example, if an available Mal-PEG has 80% terminal activity such that 80% of the PEGs are functionalized with Mal, and the Mal-PEG is used in 20-fold molar excess over hemoglobin, then this molar ratio can be expressed as a 16-fold molar excess of Mal-PEG over hemoglobin based on 100% terminal activity.

"Thiolation" refers to a process that increases the number of sulfhydryl groups on a molecule. For example, reacting a protein with 2-iminothiolane ("2-IT") converts free amines on the surface of the protein to sulfhydryl groups. These sulfhydryl groups are then available for reaction with a thiol reactive moiety, such as a maleimide.

"Unliganded hemoglobin" refers to any hemoglobin containing at least one heme moiety that is not liganded to a molecular gas such as oxygen, carbon monoxide or nitric oxide. As such, the hemoglobin is considered "unliganded" if only one of the heme moieties is not liganded to a molecular gas.

The term "SVA-PEG-Hb" as used herein refers to Hb to which mPEG-SVA has been conjugated.

Having described the invention in detail, it will be apparent that modifications and variations are possible without departing from the scope of the invention defined in the appended claims.

EXAMPLES

The following non-limiting examples are provided to further illustrate the present invention.

Example 1—Preparation of SVA-PEG-Hb

Packed red blood cells ("RBCs") are procured from a commercial source, such as from a local Blood Bank, the New York Blood Center, or the American Red Cross. The material is obtained not more than 45 days from the time of collection. All units are screened for viral infection and subjected to nucleic acid testing prior to use. Non-leukodepleted pooled units are leukodepleted by membrane filtration to remove white blood cells. Packed RBCs are pooled into a sterile vessel and stored at 2-15° C. until further processing. The volume is noted, and Hb concentration is determined using a commercially available co-oximeter, or other art-recognized method.

RBCs are washed with six volumes of 0.9% sodium chloride using a 0.45-µm tangential flow filtration, followed by cell lysis by decreasing the concentration of salt. Hb extraction is performed using the same membrane. The cell wash is analyzed to verify removal of plasma components by a spectrophotometric assay for albumin. The lysate is processed through a 0.16-µm membrane in the cold to purify Hb. The purified Hb is collected in a sterile depyrogenated and then ultrafiltered to remove virus. Additional viral-reduction steps, including solvent/detergent treatment, nanofiltration, and anion Q membrane purification may be performed. All steps in this process are carried out at 2-15° C.

Hb from lysate is exchanged into Ringer's lactate ("RL"), or phosphate-buffered saline ("PBS", pH 7.4), using a 30-kD membrane. The Hb is concentrated to 1.1-1.5 mM (in tetramer). Ten to 12 volumes of RL or PBS are used for solvent exchange. This process is carried out at 2-15° C. The pH of the solution prepared in RL or PBS is adjusted to 8.0 prior to thiolation. The Hb is sterile-filtered through a 0.45 or 0.2-µm disposable filter capsule and stored at 4±2° C. before the chemical modification reaction is performed.

PEG Conjugation:

mPEG-SVA (Laysan Bio, Inc., Arab, Ala.) was conjugated to the SFH using a 10-fold molar excess of mPEG-SVA based on 100% terminal activity over the starting tetrameric Hb concentration. The Hb was first allowed to equilibrate with the atmosphere to oxygenate the Hb. Approximately 1 mM Hb in RL (pH 7.0-8.5), PBS, or any similar buffer was combined with 10 mM mPEG-SVA in the same buffer. This mixture was stirred continuously for about 2 hours at 10±5° C.

The resulting PEG-Hb conjugate was processed through a 70-kD membrane (i.e. <10 diavolume filtration) to remove unreacted reagents. This process was monitored by size-exclusion liquid chromatography ("LC") at 540 nm and 217 nm. The concentration was adjusted to 4 g/dl Hb and the pH was adjusted to a range from 6.0 to 7.8, or 7.0±1.0.

The PEG-Hb conjugate was sterile filtered using a 0.2-µm sterile disposable capsule and collected into a sterile depyrogenated vessel at 4±2° C. The PEG-Hb conjugate was diluted to 4.4 g/dL in RL and the pH adjusted to 7.4±0.2 and then sterile-filtered (0.2 µm) and aliquoted into endotoxin free sterile containers.

The final PEGylated hemoglobin conjugate ("SVA-PEG-Hb" or "SP4") had the properties shown in Table 1:

TABLE 1

| Properties of PEG-ββ-Hb | |
|---|---|
| Properties | Values |
| Hb Concentration (g/dL) | 4.4 |
| pH | 7.4 |
| Degree of PEGylation | 8-9 |
| COP (mmHg) | 85 |
| P50 (mmHg) | 7 |
| Hill number (n-value) | 1.1 |

The structure of SVA-PEG-Hb was further confirmed via standard methodology.

Example 2—Stability Testing of SVA-PEG-Hb

SVA-PEG-Hb of Example 1 was analyzed via non-dissociating size exclusion chromatography (LC) as compared to the MalPEG-Hb (known as MP4) and to SFH. These results are depicted in FIG. 4. This figure suggests that SVA-PEG-Hb is a more homogeneous product than MP4.

FIG. 5 is a LC analysis under high-salt, dissociating conditions (0.9M $MgCl_2$) of SVA-PEG-Hb liganded to CO (SP4CO, bottom) as compared to a form of MP4 liganded to CO (MP4CO, top) under accelerated storage conditions at 40° C. for up to one month. The chromatogram shows that SP4CO retained greater stability upon such accelerated stability testing than did MP4CO.

FIG. 6 is a LC analysis under high-salt, dissociating conditions (0.9M MgCl$_2$) of SVA-PEG-Hb liganded to CO (SP4CO, bottom) as compared to NPC-PEG-Hb liganded to CO (NP4CO, top) under accelerated storage conditions at 32° C. for 9 days. This chromatogram shows that SP4CO retained greater stability upon such accelerated stability testing than did NP4CO. The chromatograms showing left-shifting peaks demonstrate the formation of higher molecular weight constituents observed for NP4CO compared to SP4CO by LC under high-salt, dissociating conditions.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description and shown in the accompanying drawings shall be interpreted as illustrative and not in a limiting sense.

What is claimed is:

1. A polyethylene glycol (PEG) hemoglobin tetramer conjugate having a P50 ranging from about 2 to about 10 mmHg as measured at 37° C. and pH 7.4, wherein the PEG hemoglobin tetramer conjugate has the structure

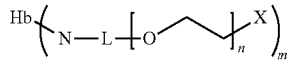

wherein:
Hb is a β,β-intramolecularly-crosslinked hemoglobin tetramer,
N is an amino group of the hemoglobin tetramer,
L is a linker —C(O)—(CH$_2$)$_p$—,
X is a terminal group,
m is the average number of activated-PEG polymers conjugated to the hemoglobin tetramer and is on average from about 6 to about 10 PEG molecules per tetramer,
n is the average number of oxyethylene units of a PEG having an average molecular weight of from about 4,000 to about 6,000 Daltons, and
p is an integer from 4 to 6.

2. The PEG hemoglobin tetramer conjugate of claim 1, prepared by a process comprising reacting the hemoglobin tetramer with at least one PEG polymer, the PEG polymer having the structure:

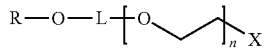

wherein R is the amino reactive moiety.

3. The PEG hemoglobin tetramer conjugate of claim 2 wherein R is succinimidyl or p-nitrophenyl.

4. The PEG hemoglobin tetramer conjugate of claim 2, wherein X is hydroxy, aryloxy, or C$_1$-C$_{20}$ alkoxy.

5. The PEG hemoglobin tetramer conjugate of claim 1, wherein a bis(3,5-dibromosalicyl) fumarate is crosslinked at the two β82 lysine residues of the hemoglobin tetramer molecule.

6. The PEG hemoglobin tetramer conjugate of claim 1, wherein the PEG hemoglobin tetramer conjugate has a colloid osmotic pressure of at least 50 mm Hg; and the PEG hemoglobin tetramer conjugate is liganded to oxygen, carbon monoxide, or nitric oxide.

7. The PEG hemoglobin tetramer conjugate of claim 1, wherein X is methoxy; m is on average from about 8 to about 9 PEG molecules per tetramer; the P50 is about 7 mmHg; and the PEG has an average molecular weight of about 5,000 Daltons.

8. The PEG hemoglobin tetramer conjugate of claim 1, wherein the PEG is methoxyPEG-succinimidyl valerate (mPEG-SVA).

9. The PEG hemoglobin tetramer conjugate of claim 1, wherein the amino reactive moiety of the PEG is conjugated to an amino moiety of the hemoglobin tetramer selected from an ε-amino moiety of a lysine residue of the hemoglobin tetramer, an α-amino moiety of a terminal valine residue of the hemoglobin tetramer, or a combination thereof.

10. The PEG hemoglobin tetramer conjugate of claim 9, wherein the amino reactive moiety of the PEG is conjugated to an α-amino moiety of a terminal valine residue of an α-subunit or β-subunit of the hemoglobin tetramer, or the amino reactive moiety of the PEG is conjugated to an ε-amino moiety of a lysine residue of the hemoglobin tetramer α-subunit or β-subunit.

11. The PEG hemoglobin tetramer conjugate of claim 10, wherein the lysine residue is a lysine residue of the hemoglobin tetramer α-subunit selected from the group consisting of lysine-7, lysine-11, lysine-16, lysine-40, lysine-56, lysine-60, lysine-61, lysine-90, lysine-99, lysine-127, lysine-139, and a combination thereof; or the lysine residue is a lysine residue of the hemoglobin β-subunit selected from the group consisting of lysine-8, lysine-17, lysine-59, lysine-61, lysine-65, lysine-66, lysine-82, lysine-95, lysine-120, lysine-132, lysine-144, and a combination thereof.

12. The PEG hemoglobin tetramer conjugate of claim 1, wherein N-ethyl maleimide is conjugated to β93 cysteine residues of the hemoglobin tetramer.

13. The PEG hemoglobin tetramer conjugate of claim 1, wherein the PEG hemoglobin tetramer conjugate has greater stability when stored at −20° C. for 36 months or at ambient temperature for at least 18 months compared to an otherwise identical hemoglobin tetramer conjugate wherein the PEG polymer is conjugated via a thiol group or a β93 cysteine residue of the hemoglobin tetramer and has the structure

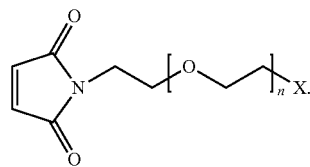

14. A pharmaceutical composition comprising the PEG hemoglobin tetramer conjugate of claim 1 and a pharmaceutically acceptable carrier.

15. A method of delivering oxygen, nitric oxide, carbon monoxide or mixtures thereof to tissue and reducing nitrite to nitric oxide (NO) in the microvasculature, the method comprising administering the PEG hemoglobin tetramer conjugate of claim 1 to a subject in need thereof, wherein following administration, the hemoglobin tetramer becomes unliganded and converts nitrite to nitric oxide in the microvasculature.

16. The PEG hemoglobin tetramer conjugate of claim 13 wherein the hemoglobin tetramer is recombinant.

17. The pharmaceutical composition of claim 14, wherein the composition is normo-oncotic with blood.

18. The pharmaceutical composition of claim 14, wherein the composition is hyperoncotic as compared to blood.

19. A method of treatment comprising administering the PEG hemoglobin tetramer conjugate of claim 1 to a subject in need thereof, wherein the treatment is for:

- acute liver failure, beta thalassemia, a burn, chronic critical limb ischemia, carbon dioxide or cyanide poisoning, chronic obstructive pulmonary disease (COPD), congestive heart failure, hypoxia, malaria, organ ischemia, peripheral vascular disease, *porphyria*, pre-eclampsia in pregnancy, sepsis, sickle cell disease, retinal disease, an intra-ocular condition, testicular torsion, trauma, shock, traumatic brain injury, ulcers, vasospasm, or a combination thereof; or
- non-traumatic hemorrhagic shock, pre-hospital setting trauma, traumatic hemorrhagic shock, acute lung injury, adult respiratory distress syndrome, traumatic brain injury, stroke, solid tumor cancer, organ degradation (ex-vivo), organ degradation (in recipient), severe sepsis, septic shock, myocardial infarction, cardiac ischemia, cardiogenic shock, acute heart failure, pulmonary embolism, or a combination thereof; or
- administering as an adjunct to angioplasty, as an adjunct for plastic surgery, or as an adjunct in implanting a ventricular assist device; as a blood substitute, a cardioprotectant, a cryopreservative, a hemodialysis adjunct, an oncology agent, an organ preservative, a performance enhancement agent, a surgery adjunct, or a wound healing agent; in imaging; to improve lung function; or a combination thereof; or
- veterinary treatment of loss of blood due to injury, hemolytic anemia, infectious anemia, bacterial infection, Factor IV fragmentation, hypersplenism and splenomegaly, hemorrhagic syndrome in poultry, hypoplastic anemia, aplastic anemia, idiopathic immune hemolytic conditions, iron deficiency, isoimmune hemolytic anemia, microangiopathic hemolytic anemia, parasitism, or surgical-anesthesia induced brain damage.

* * * * *